United States Patent [19]

Sano et al.

[11] Patent Number: 5,057,541
[45] Date of Patent: Oct. 15, 1991

[54] COMPOSITION FOR EXTERNAL APPLICATION

[75] Inventors: Tomohiko Sano, Funabashi; Yuji Suzuki, Sakura; Kayoto Iwata, Matsudo, all of Japan

[73] Assignee: Kao Corporation, Tokyo, Japan

[21] Appl. No.: 281,854

[22] Filed: Dec. 9, 1988

[30] Foreign Application Priority Data

Dec. 11, 1987 [JP] Japan ................................ 62-313836

[51] Int. Cl.$^5$ ............................................. A61K 47/00
[52] U.S. Cl. ..................................... 514/772; 514/110; 514/148; 514/937
[58] Field of Search ................ 514/143, 148, 772, 110

[56] References Cited

FOREIGN PATENT DOCUMENTS 2174100 10/1986 United Kingdom .

OTHER PUBLICATIONS

Balsam et al., Cosmetics, Science 2 Technology, vol. 1, pp. 12–16 (1976).
Chemical Abstracts 106: 20335y, 1987.
Chemical Abstracts 109: 155973n, 1988.

*Primary Examiner*—Leonard Schenkman
*Attorney, Agent, or Firm*—Oblon, Spivak, McClelland, Maier & Neustadt

[57] ABSTRACT

An emulsion-like or creamy composition for external application is disclosed. The composition is prepared by applying a shear force to an aqueous suspension comprising 0.1 to 20% by weight of one or more specific types of polyvalent metal alkyl phosphates. This composition has a gloss and a beautiful outward appearance, in which a powdery polyvalent metal alkyl phosphate is dispersed in an aqueous medium. The composition exhibits favorable characteristics inherent to a powder such as excellent extendability, good smoothness, stickilessness, slipperiness as well as superior freshness.

13 Claims, No Drawings

COMPOSITION FOR EXTERNAL APPLICATION

BACKGROUND OF THE INVENTION

1. Field of the Invention

This invention relates to a composition for external application, and, more particularly, to a composition in a form of an emulsion or cream, in which characteristics inherent to a powder are fully exhibited. The composition can be used for external application, for example, as a skin cosmetic, providing an excellent feeling upon use.

2. Description of the Background

Make-up cosmetics, oily cosmetics into which powders are formulated, carmine lotions, and the like are given as compositions for external application utilizing characteristics inherent in powders.

In many of the cases, however, formulating powders into an oily cosmetic greatly diminishes favorable characteristics possessed by powders such as excellent smoothness and extendability, moderate adherence, freshness, a good feeling on use, and the like. In carmine lotions, powders are stably dispersed into liquid only with difficulty, making precipitation of powders unavoidable during storage. This entails the nuisance of having to shake a carmine lotion for dispersing powders when used. To avoid this kind of nuisance, only very limited types of powders can be used for carmine lotions. In particular, no hydrophobic powder can be used in a system such as a carmine lotion.

In view of this situation the present inventors have undertaken extensive studies to resolve the above-mentioned problem. As a result, the inventors have found that dispersing a polyvalent metal alkyl phosphate, which is a kind of hydrophobic powder, into an aqueous medium and providing a shear force to the aqueous suspension provided an emulsion-like or creamy composition for external application, in which the above-mentioned favorable characteristics inherent to powders were completely preserved.

SUMMARY OF THE INVENTION

Accordingly, an object of this invention is to provide an emulsion-like or creamy composition for external application prepared by applying a shear force to an aqueous suspension comprising 0.1 to 20% by weight of one or more polyvalent metal alkyl phosphates.

A more specific object of this invention is to provide said emulsion-like or creamy composition having a viscosity of 0.1 poise or more at 30° C.

Other objects, features and advantages of the invention will hereinafter become more readily apparent from the following description.

DETAILED DESCRIPTION OF THE INVENTION AND PREFERRED EMBODIMENTS

The polyvalent metal alkyl phosphate used as a powder component of the composition of this invention is prepared, for example, by the reaction of (1) an alkyl phosphate represented by the following formula (I) or (II):

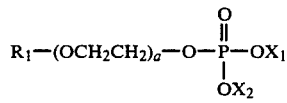
(I)

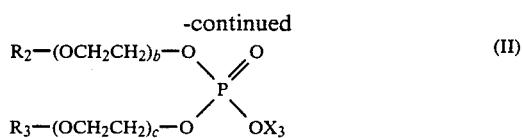

wherein $R_1$, $R_2$, and $R_3$ independently represent a linear or branched, saturated or unsaturated hydrocarbon group having a $C_{4-38}$ carbon atom content; $X_1$, $X_2$, and $X_3$ independently represent a hydrogen atom, an alkali metal, or an amine; and a, b, and c independently represent an integer of 0 to 10; and (2) a metal salt represented by the following formula (III):

$$M_m Y_n \quad (III)$$

wherein M represents a metal other than an alkali metal, Y represents an organic or inorganic anion, and m and n each represent an integer corresponding to the valence of Y and M.

More specifically, the reaction of a compound having an alkali metal or an amine for $X_1$, $X_2$, and $X_3$ in the above formula (I) or (II) with a compound of formula (III) according to a process disclosed in -Japanese Patent Publication No. 12646/1967 or Japanese Patent Application Laid-open No. 84919/1978 produces compounds of the following formula (IV) or (V):

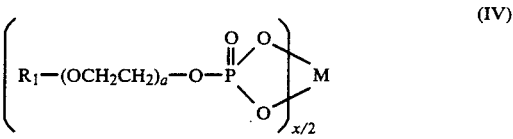

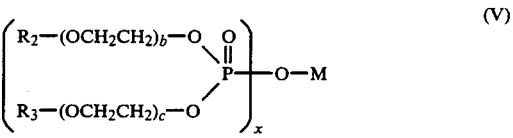

wherein x represents the valence of M; and $R_1$, $R_2$, $R_3$, M, a, b, and c have the same meanings as defined above.

$R_1$, $R_2$, and $R_3$ in formulae (I) and (II) are hydrocarbon groups having 4 to 38 carbon atoms. Those having carbon atoms of 8 or more are especially preferable. If the carbon atom content of the hydrocarbon groups is less than 4, metal salts of the alkyl phosphate become too viscous, rendering a lower smoothness and extendability, sometimes providing only insufficient water-repellence. Given as examples of favorable hydrocarbon groups are octyl, nonyl, decyl, dodecyl, undecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, octenyl, nonenyl, decenyl, dodecenyl, undecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, hentriacontenyl, dotriacontenyl, octadienyl, nonadienyl, decadienyl, dodecadienyl undecadienyl, tridecadienyl, tetradecadienyl, pentadecadienyl, hexadecadienyl, heptadecadienyl, octadecadienyl, nonadecadienyl, eicosadienyl, heneicosadienyl, docosadienyl, tricosadienyl, tetracosadienyl, pentacosadienyl, hexacosadienyl, heptacosadienyl, octacosadienyl, nonacosadienyl, triacontadienyl, hentriacontadienyl, dotriacontadienyl, 2-hexyldecyl, 2-octylundecyl, 2-decyltetradecyl, 2-undecylhexadecyl, 2-tetradecyloctadecyl, and the like.

Alkali metals such as potassium, sodium, and the like, and amines, including monoethanolamine, diethanolamine, triethanolamine, triisopropanolamine, morphorine, arginine, and the like, are given as preferable groups represented by $X_1$, $X_2$, and $X_3$ in formulae (I) and (II).

M in formula (III) represents a metal other than an alkali metal, and includes alkali earth metals such as Mg, Ca, Sr, Ba, and the like; bivalent transition metals such as Zn, Cu, Ni, Co, Fe, Mn, Cd, Pb, Cr, Ti, and the like; as well as Al and the like. Among these especially preferable metals are Ca, Mg, Ba, Zn, and Al. Given as examples of Y in formula (III) are inorganic anions, such as halogens, $SO_4$, $NO_3$, $CO_3$, $PO_4$, and OH; and organic carboxylic acid anions such as acetic acid, propionic acid, citric acid, and the like. Among these, particularly preferable anions are halogens, $SO_4$, $PO_4$, $NO_3$, and $CO_3$. As a metal salt represented by formula (III), a water soluble one is preferable. Particularly preferable metal salts are $CaCl_2$, $MgCl_2$, $FeCl_2$, $ZnCl_2$, $ZnSO_4$, $MgSO_4$, $FeSO_4$, $Ni(NO_3)_2$, and the like.

Besides polyvalent metal alkyl phosphates, various components may be formulated into the composition for external application of the present invention as appropriate, including various kinds of cosmetic oils, surface active agents, humectants, antiseptics, antioxidants, perfumes, and the like. Given as examples of cosmetic oils are liquid paraffin, petrolatum, paraffin wax, squalane, ceresine wax, bees wax, carnauba wax, candelilla wax, hydrogenated castor oil, olive oil, lanolin, lanolin alcohol, higher alcohols, fatty acids, synthetic esters made from a higher alcohol and a fatty acid, silicones, and the like. A cationic, anionic, amphoteric, or nonionic surface active agent can be formulated into the composition of this invention for the purpose of enhancing its stability.

Nonionic surface active agents, water soluble polyoxyethylenealkyl ether in particular, are preferable surface active agents. Such a surface active agent can be added to the composition of this invention by adding the same into an aqueous medium before or after a polyvalent metal alkyl phosphate is added. The the addition method particularly preferable for ensuring the stability of the composition and for providing a good feeling on use, however, is to add a surface active agent into either an alkyl phosphate aqueous solution or a metal salt aqueous solution in advance, and then to mix the two solution to form a polyvalent metal alkyl phosphate in the presence of such a surface active agent.

Given as other nonionic surface active agents which can be used are polyoxyethylene fatty acid ester, polyoxyethylenesorbitan fatty acid ester, sorbitan fatty acid ester, glycerin fatty acid ester, polyoxyethylene hydrogenated castor oil, polyoxyethylenesorbitol fatty acid ester, and the like. Those nonionic surface active agents having an HLB value of 8 or more are preferable.

Humectants which may be used include, for example, sorbitol, glycerol, propylene glycol, 1,3-butylene glycol, lactic acid, sodium lactate, polyethylene glycol, and the like. Antiseptics include p-oxyalkyl benzoate, sodium benzoate, potassium sorbate, phenoxy ethanol, and the like. Named as examples of antioxidants which can be used are tocopherol, sesamol, sesamolin, lecithin, and the like.

Also, the composition of the present invention can be used as a medicine for external application which can be applied with ease providing an excellent feeling on use if a water soluble or water dispersible medicinal agent is formulated into it.

As previously mentioned a surface active agent which is commonly used in a conventional aqueous dispersion system for promoting its stability can be formulated into the composition of this invention. For the purpose of maintaining freshness inherent to powders, preserving, at the same time, water-repellence of an insoluble metal salt, however, a concentration of a surface active agent as low as possible is desirable.

With respect to an oil cosmetic, the use of this component in an amount as small as possible is desirable. Although a cosmetic oil is formulated for the purpose of promoting the feeling of the composition upon use through the reduction of flaky feeling inherent to a powder, too much use of the same may impair the freshness and smoothness which are the advantages of a powder. For this reason, use of a cosmetic oil in an amount as small as possible is desirable. The composition of this invention is particularly suitable as a cosmetic for use in summer. A UV light absorbing agent conventionally used for such a cosmetic can be formulated into the composition of this invention directed toward summer use.

The composition for external application of this invention can be prepared by adding one or more polyvalent metal alkyl phosphates and other optional ingredients to an aqueous medium for solution or dispersion, and by applying a shear force to the solution or the dispersion through mixing or the like procedure by means of a disper, a homogenizer, or the like. It is possible to add an alkyl phosphate of formula (I) or (II) and a metal salt of formula (III) to an aqueous medium to produce a polyvalent metal alkyl phosphate in the medium.

Water, a mixture of water and a polyol such as glycerol, propylene glycol, or the like, or a mixture of water and a lower alcohol such as ethanol, isopropanol, or the like can be used as an aqueous medium. Among these, a mixture of water and ethanol is preferable in view of the excellent dispersing ability of a polyvalent metal alkyl phosphate and the superior freshness of the produced composition.

Proportions, in terms of a normal range as well as a preferable range of polyvalent metal alkyl phosphates, optional ingredients, and aqueous media in the composition are given below:

|  | Proportions (% by weight) | |
| --- | --- | --- |
|  | Normal Range | Preferable Range |
| Polyvalent metal alkyl phosphate | 0.1–20 | 0.5–10 |
| Surface active agent | 0–10 | 0.1–3 |
| Cosmetic oil | 0–10 | 0.5–5 |
| Humectant, medicinal component, etc. | 0–20 | 0–10 |
| Ethanol | 0–30 | 0.5–10 |
| Water | 15–99 | 62–95 |

It is desirable that the composition for external application of this invention have a viscosity of 0.1 poise or more, preferably of 100 to 10,000 poise, as measured by a rotating viscosimeter, e.g. a B-type viscosimeter, at 30° C.

The composition for external application of this invention is an emulsion-like or creamy substance having a gloss and a beautiful outward appearance, in which a powdery polyvalent metal alkyl phosphate is dispersed in an aqueous medium. The composition exhibits favorable characteristics inherent to a powder such as excellent extendability, good smoothness, stickilessness, slipperiness as well as superior freshness.

Other features of the invention will become apparent in the course of the following description of the exemplary embodiments which are given for illustration of the invention and are not intended to be limiting thereof.

EXAMPLES

Example 1

To 30 ml of water 5 g of monosodium monolauryl phosphate (molecular weight: 288) was added and stirred at 40° C. Separately, 0.96 g of anhydrous calcium chloride was dissolved into 70 ml of water, and this latter solution was added dropwise into said monosodium monolauryl phosphate solution over 30 minutes while stirring. Dispersion was effected using a disper at 40° C. for 1 minute, and then the dispersed mixture was allowed to cool to room temperature while stirring to produce a white, glossy, homogeneous creamy cosmetic composition having a viscosity of 1,500 poise at 30° C. The product possessed good stability, exhibited superior extendability and freshness, and provided a good feeling upon use.

As separate experiments, several creamy cosmetic compositions containing different polyvalent metal alkyl phosphates were produced. This was done by producing different types of polyvalent metal alkyl phosphates from monosodium monolauryl phosphate, monosodium monocetyl phosphate, and monosodium monostearyl phosphate through reaction of each of these phosphates with an equivalent amount of calcium chloride, magnesium chloride, or zinc chloride. The same procedure as above was followed for producing creamy cosmetic compositions.

These creamy cosmetic compositions were evaluated by 10 expert panelists in terms of extendability, moistness, slipperiness, and freshness. The results are shown in Table 1, in which figures represent the values obtained by averaging the evaluation by the 10 panelists according to the following standard:

Excellent: +2
Pretty well: +1
Normal: 0
Modest: −1
Bad: −2

TABLE 1

| Alkyl phosphate | Metal | Extendibility | Moistness | Slipperiness | Freshness |
| --- | --- | --- | --- | --- | --- |
| Monolauryl phosphate | Ca | +2 | +1.3 | +2.0 | +1.7 |
|  | Mg | +2 | +1.4 | +1.5 | +1.8 |
|  | Zn | +2 | +1.7 | +2.0 | +1.8 |
| Monocetyl phosphate | Ca | +2 | +1.4 | +2.0 | +2.0 |
|  | Mg | +2 | +1.5 | +1.7 | +2.0 |
|  | Zn | +2 | +1.5 | +2.0 | +2.0 |
| Monostearyl phosphate | Ca | +2 | +1.5 | +2.0 | +2.0 |
|  | Mg | +2 | +1.7 | +1.9 | +2.0 |
|  | Zn | +2 | +1.7 | +2.0 | +2.0 |

Example 2

Monosodium monocetyl phosphate and magnesium chloride were reacted in the same manner as in Example 1, and the resulting product was washed with a water-/ethanol (1/1) mixture, followed by filtration and drying of the residue. Five (5) g of the magnesium monocetyl phosphate ($C_{32}H_{58}P_2O_8Mg$) thus produced was slowly added into 100 ml of a 10% ethanol aqueous solution while agitating with a disper to produce a white, glossy, homogeneous creamy cosmetic composition having a viscosity at 30° C. of 1,000 poise. This product was stable and exhibited superior extendability and freshness, and provided a good feeling upon use.

The same type of creamy cosmetic compositions were prepared using polyvalent metal alkyl phosphates listed in Table 2, instead of monosodium monocetyl phosphate, and were evaluated in the same manner as in Example 1. The results are shown in Table 2.

TABLE 2

| Alkyl phosphate | Metal | Extendibility | Moistness | Slipperiness | Freshness |
| --- | --- | --- | --- | --- | --- |
| Monolauryl phosphate | Ca | +2.0 | +1.6 | +2.0 | +2.0 |
|  | Mg | +2.0 | +1.5 | +1.7 | +2.0 |
|  | Zn | +2.0 | +1.5 | +1.5 | +2.0 |
| Monocetyl phosphate | Ca | +2.0 | +1.4 | +1.7 | +2.0 |
|  | Mg | +2.0 | +1.5 | +1.9 | +2.0 |
|  | Zn | +2.0 | +1.7 | +2.0 | +2.0 |
| Monostearyl phosphate | Ca | +2.0 | +1.5 | +1.8 | +2.0 |
|  | Mg | +2.0 | +1.8 | +2.0 | +2.0 |
|  | Zn | +2.0 | +1.7 | +2.0 | +2.0 |

Example 3

To 40 ml of water 5 g of disodium monocetyl phosphate (molecular weight: 366) was added and stirred at 40° C. Separately, 5.5 g of $ZnSO_4.7H_2O$ (molecular weight: 288) was dissolved into 60 ml of water, and this latter solution was added dropwise into said disodium monocetyl phosphate solution over 30 minutes while stirring. Dispersion of this mixture was effected using a disper at 40° C. for 1 minute, and then the dispersed mixture was allowed to cool to room temperature while stirring, followed by defoaming to produce a white, glossy, homogeneous creamy cosmetic composition having a viscosity of 800 poise at 30° C. The product possessed good stability, exhibited superior extendability and freshness, and provided a good feeling upon use. The skin felt very smooth after application of this product.

As separate experiments, several creamy cosmetic compositions containing different polyvalent metal alkyl phosphates were produced. This was done by producing different types of polyvalent metal alkyl phosphates from disodium monocetyl phosphate, disodium monomyristyl phosphate, and disodium monostearyl phosphate through reaction of each of these phosphates with an equivalent amount of divalent metal (calcium, magnesium, or zinc) sulfate. The same procedure as above was followed for producing creamy cosmetic compositions.

These creamy cosmetic compositions were evaluated in the same manner as in Example 1. The results are shown in Table 3.

TABLE 3

| Alkyl phosphate | Metal | Extendi-bility | Moist-ness | Slipper-iness | Freshness |
|---|---|---|---|---|---|
| Monocetyl phosphate | Ca | +1.5 | +1.3 | +1.2 | +2.0 |
|  | Mg | +1.7 | +1.4 | +1.5 | +2.0 |
|  | Zn | +1.8 | +1.4 | +1.3 | +2.0 |
| Monomyristyl phosphate | Ca | +1.8 | +1.4 | +1.3 | +2.0 |
|  | Mg | +1.6 | +1.5 | +1.5 | +2.0 |
|  | Zn | +1.5 | +1.2 | +1.8 | +2.0 |
| Monostearyl phosphate | Ca | +1.7 | +1.2 | +1.4 | +2.0 |
|  | Mg | +1.9 | +1.2 | +1.5 | +2.0 |
|  | Zn | +1.6 | +1.2 | +1.3 | +2.0 |

Example 4

Preparation of a powder dispersed creamy cosmetic:

| <Formulation> | |
|---|---|
| Component | Amount (% by weight) |
| (1) Sodium monolauryl phosphate | 3.0 |
| (2) Sodium monocetyl phosphate | 2.0 |
| (3) Calcium dicetyl phosphate | 1.0 |
| (4) Ethanol | 10.0 |
| (5) Glycerol | 3.0 |
| (6) Calcium chloride | 0.91 |
| (7) Hydrogenated polyoxyethylene castor oil (20 E.O.) | 0.1 |
| (8) Perfume | 0.1 |
| (9) Antiseptic | 0.01 |
| (10) Purified water | 79.88 |
| Total | 100.0 |

Components (1) and (2) were dissolved into 40 g of purified water (10) at 40° C. Component (3) was homogeneously dispersed into the solution. To this dispersion was added dropwise a solution of components (4) to (9), and the remaining purified water (10), and powdery components were dispersed with a disper for 1 minute. The product was cooled until it defoamed.

The product thus produced had a viscosity at 30° C. of 1,530 poise, was stable, and provided a good feeling upon use.

In this formulation the amount of component (6) is equivalent to the amount of component (1) plus (2).

Example 5

Preparation of a powder-dispersed lotion:

| <Formulation> | |
|---|---|
| Component | Amount (% by weight) |
| (1) Calcium lauryl phosphate | 0.1 |
| (2) Aluminum stearyl phosphate | 0.1 |
| (3) Aluminum monocetyl phosphate | 0.3 |
| (4) Calcium monolauryl phosphate | 0.1 |
| (5) Ethanol | 5.0 |
| (6) Sorbitane polyoxyethylene monostearate (20 E.O.) | 0.2 |
| (7) Polyoxyethylene lauryl ether (23 E.O.) | 0.1 |
| (8) Glycerol | 5.0 |
| (9) Squalane | 5.0 |
| (10) Dimethylpolysiloxane | 2.0 |
| (11) Perfume | Suitable amount |
| (12) Antiseptic | Suitable amount |
| (13) Purified water | Balance |
| Total | 100.0 |

Components (1) to (8) were dispersed into purified water (13) using a disper, and then components (9) to (12) were slowly added to the dispersion.

The product was a stable lotion and provided a good feeling upon use.

In this formulation the amount of component (6) is equivalent to the amount of component (1) plus (2).

Example 6

Preparation of a powder-dispersed anti-sunburn cosmetic:

| <Formulation> | |
|---|---|
| Component | Amount (% by weight) |
| (1) Disodium monocetyl phosphate | 5.0 |
| (2) Calcium monocetyl phosphate | 1.0 |
| (3) Zinc monolauryl phosphate | 1.0 |
| (4) Ethanol | 10.0 |
| (5) Glycerol | 5.0 |
| (6) Sorbitol | 1.0 |
| (7) Liquid paraffin | 3.0 |
| (8) MgCl.6H$_2$O | 2.8 |
| (9) Antiseptic | Suitable amount |
| (10) UV light absorber * | 1.0 |
| (12) Purified water | Balance |
| Total | 100.0 |

*Parsol MCX (p-methoxy cinnamate, manufactured by Givaudan S.A.)

Components (1) to (6) were dissolved into 40 g of purified water (11) at 40° C. To the solution were added dropwise a solution of components (7) to (10) in the remaining purified water (11) while stirring. The powdery components were dispersed with a disper for 1 minute, and the product was allowed to cool.

The product thus produced was a white creamy suspension with a viscosity at 30° C. of 1,000 poise, was stable, exhibited excellent extendability, and provided a slippery, fresh feeling upon use.

In this formulation the amount of component (8) used was equivalent to the amount of component (1).

Example 7

Preparation of a powder-dispersed sebum-absorptive cosmetic:

| <Formulation> | |
|---|---|
| Component | Amount (% by weight) |
| (1) Calcium monocetyl phosphate | 5.0 |
| (2) Calcium monolauryl phosphate | 5.0 |
| (3) Polyoxyethylene octyldodecyl ether (20 E.O.) | 2.0 |
| (4) Benthonite | 10.0 |
| (5) Antiseptic | Suitable amount |
| (6) Purified water | Balance |
| Total | 100.0 |

Components (3) and (5) were dissolved under heating into a half amount of purified water (6). To the solution were added components (1), (2), and (4), and the mixture was thoroughly dispersed with a disper. Upon confirmation of the complete dispersion, the remaining purified water (6) was slowly added while stirring. The product was slowly cooled under stirring.

The product thus produced had a viscosity at 30° C. of 3,000 poise, and exhibited an excellent sebum-absorptive performance in the evaluation by 10 expert female panelists, aged between 20 and 30, with oleaginous skin.

EXAMPLE 8

Preparation of a powder dispersed cosmetic having a foundational effect:

| <Formulation> | |
|---|---|
| Component | Amount (% by weight) |
| (1) Calcium monocetyl phosphate | 2.0 |
| (2) Calcium monostearyl phosphate | 2.0 |
| (3) Zinc stearate | 2.0 |
| (4) Polyoxyethylene lanolin (20 E.O.) | 2.0 |
| (5) Talc | 1.0 |
| (6) Spherical silica | 1.0 |
| (7) Glycerol | 1.0 |
| (8) Squalane | 2.0 |
| (9) Antiseptic | Suitable amount |
| (10) Purified water | Balance |
| Total | 100.0 |

Components (4) and (7) were dissolved under heating into purified water (10). To the solution were added components (1), (2), (3), and (5) and (6), and the mixture was thoroughly dispersed with a disper. Components (8) and (9) were slowly added while stirring. The product was cooled under continued stirring.

The product thus produced had a viscosity at 30° C. of 2,000 poise, was stable, exhibited an excellent foundational effect, and provided a superior feeling.

Example 9

Preparation of a make-up cosmetic:

| <Formulation> (amount (% by weight) | | | |
|---|---|---|---|
| Component | Cream foundation | Eye liner | Eye shadow |
| (1) Sodium monolauryl phosphate | 3.0 | 3.0 | 3.0 |
| (2) Sodium monocetyl phosphate | 2.0 | 2.0 | 2.0 |
| (3) Sodium dicetyl phosphate | 1.0 | 1.0 | 1.0 |
| (4) Ethanol | 10.0 | 10.0 | 10.0 |
| (5) Glycerol | 3.0 | 3.0 | 3.0 |
| (6) Calcium chloride | 0.91 | 0.91 | 0.91 |
| (7) Hydrogenated polyoxyethylene castor oil (20 E.O.) | 0.1 | 0.1 | 0.1 |
| (8) Perfume | 0.1 | 0.1 | 0.1 |
| (9) Antiseptic | 0.01 | 0.01 | 0.01 |
| (10) Purified water | 69.88 | 69.88 | 64.88 |
| (11) Titanium oxide | 5.0 | — | — |
| (12) Talc | 1.0 | — | 7.6 |
| (13) Red iron | 1.2 | — | — |
| (14) Yellow iron | 2.6 | — | — |
| (15) Black iron | 0.2 | 10.0 | 0.7 |
| (16) Titanium mica | — | — | 5.0 |
| (17) Ultramarine | — | — | 1.7 |
| Total | 100.0 | 100.0 | 100.0 |

Components (1) and (2) were dissolved into 40 g of purified water (10) at 40° C. Component (3) was homogeneously dispersed into the solution. To this dispersion was added dropwise a solution of components (5) to (9) and the remaining purified water (10), and the mixture was dispersed with a disper for 1 minute. This dispersion was mixed with components (11) to (17) which were dispersed into ethanol (4) and the powders in the mixture were homogeneously dispersed under agitation. The product was charged into a glass container and allowed to cool at room temperature.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent:

1. An emulsion-like or creamy composition for external application, comprising water and 0.1 to 20% by weight of a metal alkyl phosphate combined in the presence of a shear force, wherein said metal alkyl phosphate consists essentially of polyvalent metal alkyl phosphates of the formulae (IV) or (V):

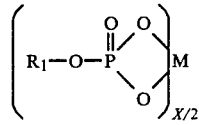 (IV)

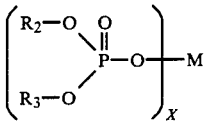 (V)

wherein $R_1$, $R_2$, and $R_3$ independently represent a linear or branched, saturated or unsaturated hydrocarbon group having 4 to 38 carbon atoms, M represents a metal other than an alkali metal and X represents the valence of M, wherein said composition is substantially free of alkali metal alkyl phosphates, ammonium alkyl phosphates, and alkanolamine alkyl phosphates.

2. The composition of claim 1, wherein M is selected from the group of Mg, Ca, Sr, Ba, Zn, Cu, Ni, Co, Fe, Mn, Cd, Pb, Cr, Ti, and Al.

3. The composition of claim 2, wherein M is selected from the group consisting of Ca, Mg, Ba, An, and Al.

4. The composition of claim 1, wherein $R_1$, $R_2$, and $R_3$ have 8 or more carbon atoms.

5. The composition of claim 1, wherein said polyvalent metal alkyl phosphate is present in an amount of 0.5-10% by weight.

6. The composition of claim 1, further comprising 0-10% by weight of a surface active agent.

7. The composition of claim 6, wherein said surface active agent is present in an amount of 0.1-3% by weight.

8. The composition of claim 1, further comprising 0-10% by weight of a cosmetic oil.

9. The composition of claim 8, wherein said cosmetic oil is present in an amount of 0.5-5% by weight.

10. The composition of claim 1, further comprising one or more ingredient selected from the group consisting of humectants and medicinal components in a total amount of 0-20% by weight.

11. The composition of claim 10, wherein said ingredient is present in a total amount of 0-10% by weight.

12. The composition of claim 1, further comprising 0-30% by weight of ethanol.

13. The composition of claim 12, wherein said ethanol is present in an amount of 0.5-10% by weight.

* * * * *